US00PP22336P3

(12) United States Plant Patent
Blom

(10) Patent No.: US PP22,336 P3
(45) Date of Patent: Dec. 13, 2011

(54) ***CHRYSANTHEMUM* PLANT NAMED ZANMUFAY**

(50) Latin Name: *Chyrsanthemum×morifolium Ramat.*
Varietal Denomination: Zanmufay

(75) Inventor: Wilhelmus Bernardus Blom, Leimuiden (NL)

(73) Assignee: Chrysanthemum Breeders Association Research B.V., Valkenburg Z-H (NL)

( * ) Notice: Subject to any disclaimer, the term of this patent is extended or adjusted under 35 U.S.C. 154(b) by 63 days.

(21) Appl. No.: 12/591,868

(22) Filed: Dec. 3, 2009

(65) Prior Publication Data

US 2011/0138511 P1 Jun. 9, 2011

(51) Int. Cl.
*A01H 5/00* (2006.01)

(52) U.S. Cl. ..... Plt./296

(58) Field of Classification Search ..... Plt./296
See application file for complete search history.

(56) References Cited

U.S. PATENT DOCUMENTS

PP20,475 P3 * 11/2009 Blom ..... Plt./290
* cited by examiner

*Primary Examiner* — Wendy C Haas
(74) *Attorney, Agent, or Firm* — Steptoe & Johnson LLP

(57) ABSTRACT

A *chrysanthemum* plant named 'Zanmufay' characterized by its medium sized blooms with bronze ray florets and prolific branching; natural season flower date October 12-16; blooming for a period of 4 weeks.

3 Drawing Sheets

Botanical designation: *Chrysanthemum×morifolium* Ramat.

Cultivar denomination: 'Zanmufay'.

BACKGROUND OF THE INVENTION

The present invention relates to a new and distinct cultivar of *chrysanthemum* plant, botanically known as *Chrysanthemum×morifolium* Ramat., and hereinafter referred to by the cultivar denomination 'Zanmufay'. 'Zanmufay' is a product of a breeding and selection program for outdoor pot mums (garden mums) which had the objective of creating new cultivars with a double type inflorescence, a natural season flower date around October 12-16, blooming for a period of 4 weeks. 'Zanmufay' is a seedling resulting from a crossing between the female parent id 4336 and male parent id 2864 (unpatented). Plants of the 'Zanmufay' differ from plants of the parents in the following characteristics. (1) color ray-florets. And (2) natural season flower date. (1) The color of the ray-florets of the seedling is orange, while this is pink in the female parent, and yellow in the male parent. (2) Plants of the new cultivar 'Zanmufay' flower two week earlier than those of the male parent.

The new and distinct cultivar was discovered and selected as a flowering plant by Wilhelmus Bernardus Blom on a cultivated field in Rijsenhout, The Netherlands in 2005. The first act of asexual production of 'Zanmufay' was accomplished when vegetative cuttings from the initial selection in 2005 were used and propagated further in a controlled environment in Rijsenhout, The Netherlands. The new cultivar has been found to retain its distinctive characteristics through successive propagations.

BRIEF DESCRIPTION OF THE DRAWINGS

The present invention of a new and distinct variety of *chrysanthemum* is shown in the accompanying drawings, the color being as nearly true as possible with color photographs of this type.

DESCRIPTION OF THE INVENTION

Figure 1:
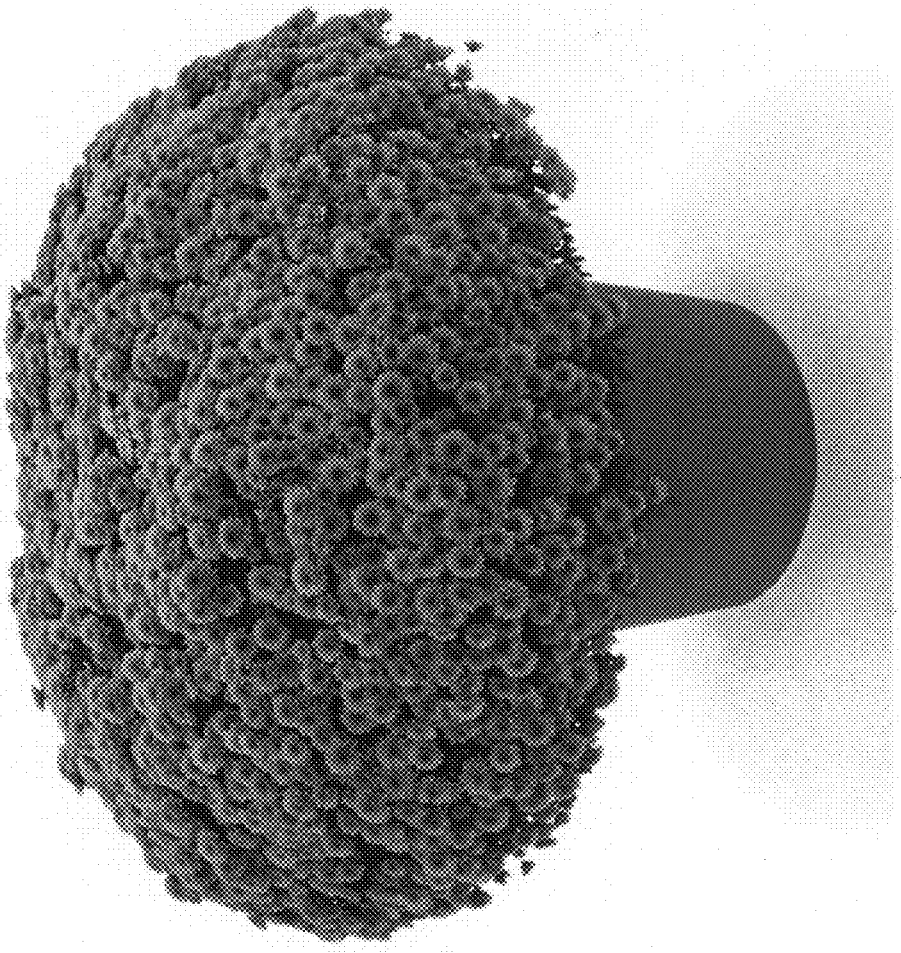
FIG. 1 shows a plant of the cultivar in full bloom.
Figure 2:
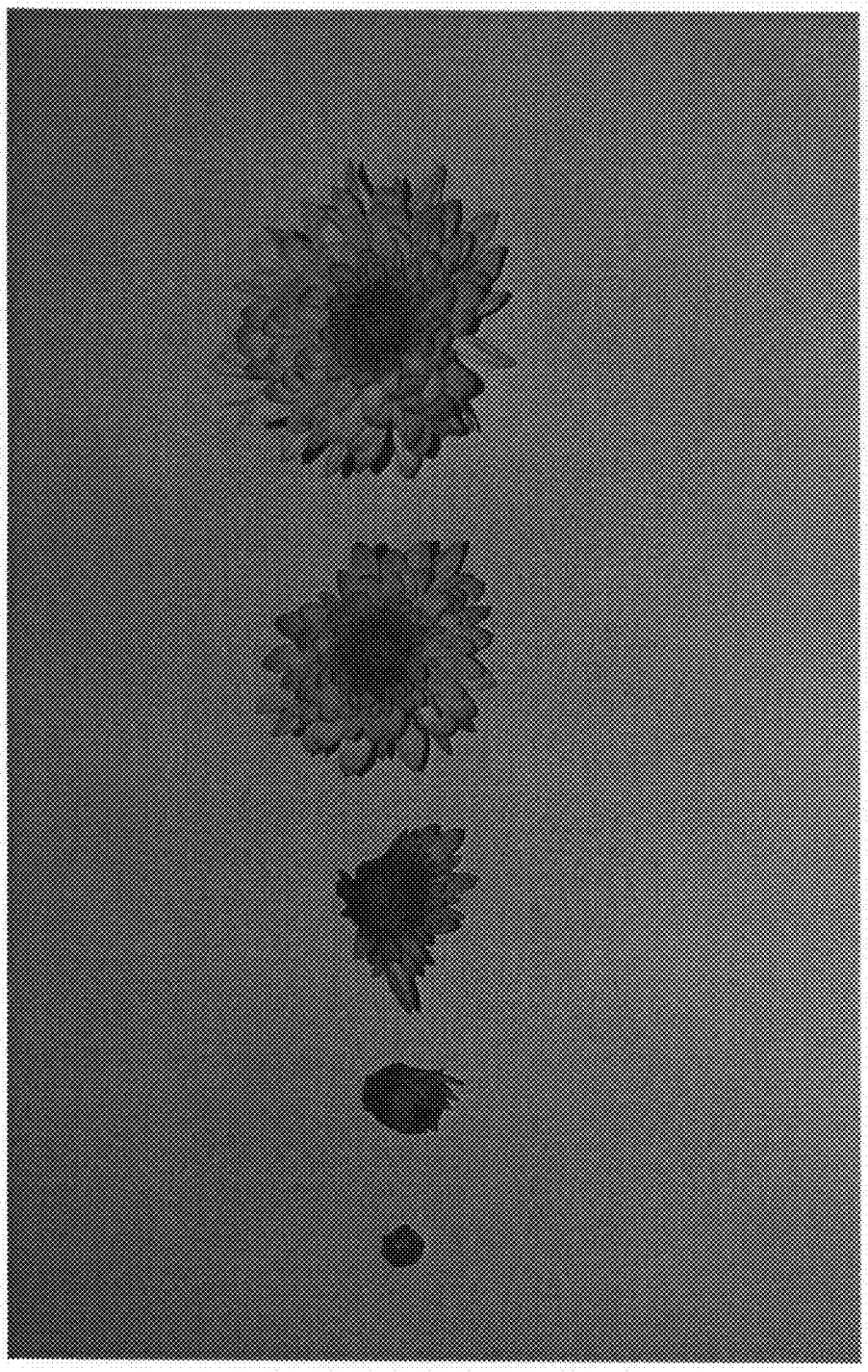
FIG. 2 shows the various stages of bloom of the new cultivar.
Figure 3:
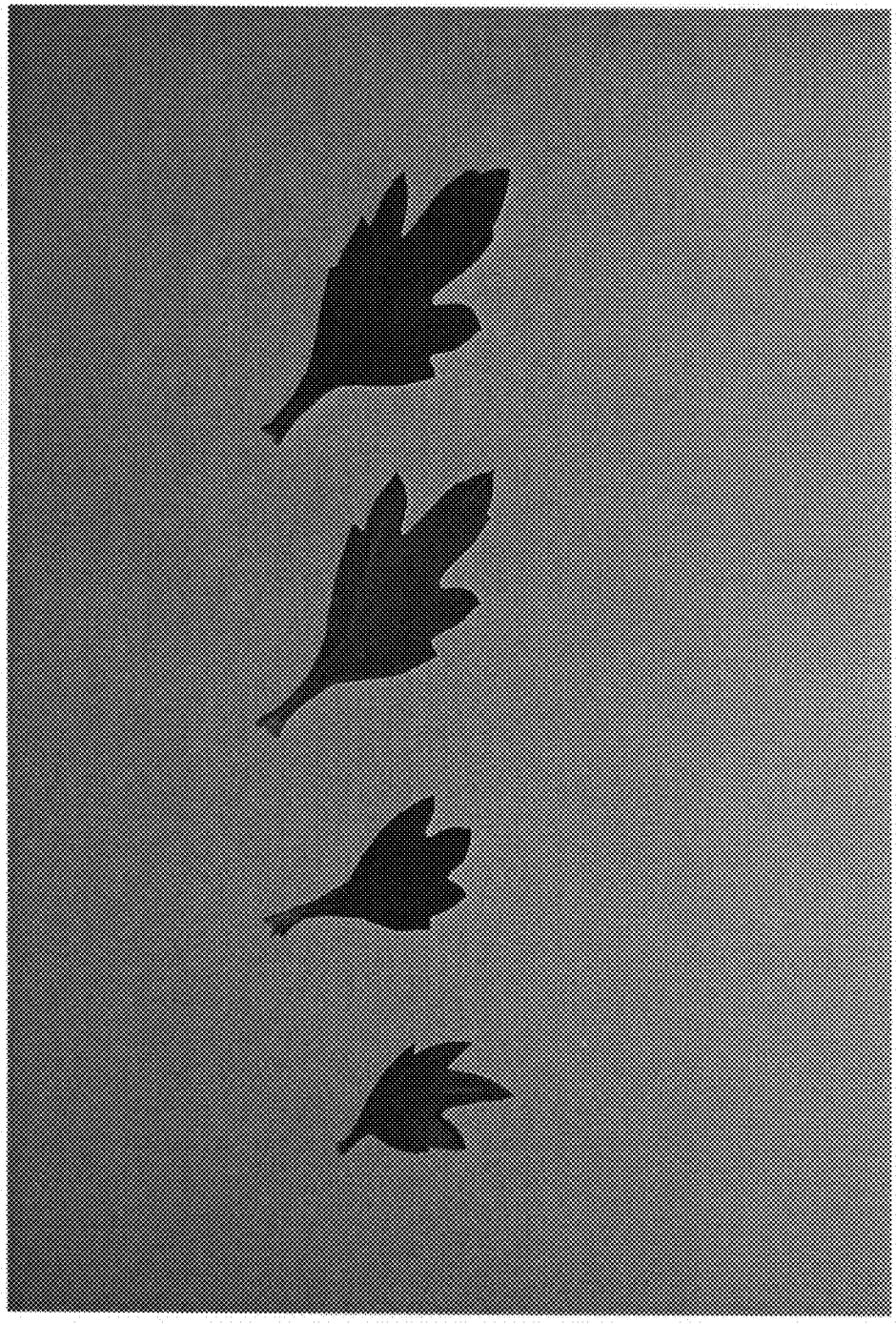
FIG. 3 shows the various stages of foliage of the new cultivar.

The observations and measurements were gathered from plants grown out door in Rijsenhout, The Netherlands under natural day length and temperature and planted in week 25 in 2009. The natural blooming date of this crop was October 12-16 . The average height of the plants was 35 cm. No growth retardants were used. No tests were done on disease or insect resistance or susceptibility. No tests were done on cold or drought tolerance. This new variety produces medium sized blooms with bronze ray florets blooming for a period of 5 weeks.

From the cultivars known to inventor the most similar existing cultivar in comparison to 'Zanmufay' is 'Zanmusunset' (U.S. Plant Pat. No. 20,475). When 'Zanmusunset' and 'Zanmufay' are being compared the following difference is noticed: The differences of 'Zanmusunset' and 'Zanmufay' are (1) Natural season flower date. And (2) vigour. (1) The plants of 'Zanmufay' flower later than those of 'Zanmusunset'. (2) The plants of 'Zanmufay' are less vigorous than those of 'Zanmusunset'.

The following is a description of the plant and characteristics that distinguish 'Zanmufay' as a new and distinct variety.

The color designations are taken from the plant itself. Accordingly, any discrepancies between the color designations and the colors depicted in the photographs are due to photographic tolerances. The color chart used in this description is: The Royal Horticultural Society Colour Chart, edition 2001.

DETAILED BOTANICAL DESCRIPTION

Bud:

*Size.*—Small; cross-section 0.5 cm, height 0.4 cm.

*Shape.*—Round.
*Texture.*—Pubescent.
*Outside color.*—Greyed-green 191A.

Phyllaries:
*Number.*—24-26, arranged in 3 rows.
*Shape.*—Elliptic.
*Apex.*—Acute.
*Base.*—Truncate.
*Margin.*—Entire.
*Color.*—Upper surface Greyed-green 191A.
*Length and width.*—5 mm, 2.5 mm.
*Texture.*—Pubescent.

Inflorescence:
*Type.*—Double.
*Height.*—1.5 cm.
*Diameter.*—4.5 cm.
*Peduncle length.*—6-8 cm.
*Peduncle color.*—Yellow-green 147C.
*Peduncle diameter.*—1.7 mm.
*Peduncle texture.*—Pubescent.
*Number per branch.*—Approx. 6 inflorescences.
*Duration of flowering.*—4 weeks.
*Seeds.*—Produced in small quantities, ovate, Greyed-brown 199A, length 1.5 mm, diameter 0.8 mm.
*Fragrance.*—Faint *chrysanthemum* odor.

Color:
*Center of inflorescence.*—Immature stage: Greyed-orange 173B. Mature stage: Greyed-orange 173B.
*Color of upper surface of the ray-florets.*—Greyed-orange 163D (base) to 163B (apex).
*Color of the lower surface of the ray-florets.*—Greyed-orange 163D (base) to 163C (apex).
*Tonality from distance.*—A garden mum with bronze flowers.
*Color of the ray-florets after aging of the plant.*—Greyed-orange 165D.

Ray florets:
*Texture.*—Upper and lower surface smooth.
*Number.*—170-190.
*Shape.*—Elliptic.
*Apex.*—Pointed.
*Base.*—Attenuate.
*Cross-section.*—Flat.
*Longitudinal axis of majority.*—Straight.
*Length of corolla tube.*—5-7 mm.
*Ray-floret margin.*—Entire.
*Ray-floret length.*—1.8-2.2 cm.
*Ray-floret width.*—4-5 mm.
*Ratio length/width.*—High.

Disc florets: Absent.

Receptacle:
*Color.*—Green 138C.
*Shape.*—Domed raised.
*Height.*—2 mm.
*Diameter.*—5 mm.

Reproductive organs:
*Androecium.*—Absent.
*Pollen.*—Absent.
*Gynoecium.*—Present on both ray and disc florets.
*Style color.*—Yellow-green 154C.
*Style length.*—3 mm.
*Stigma color.*—Yellow 7A.
*Stigma width.*—1 mm.
*Ovary.*—Enclosed in calyx.

Plant:
*Form.*—Grown as a spray type pot mum, color raised and mounded.
*Growth habit.*—Spherical shape.
*Growth rate.*—Vigorous.
*Height.*—35 cm.
*Width.*—45 cm.
*Stem color.*—Greyed-brown 199A.
*Stem strength.*—Weak.
*Stem brittleness.*—Brittle.
*Stem anthocyanin coloration.*—Not observed.
*Internode length.*—1.5-2.5 cm.
*Length of lateral branch.*—From top to bottom 17 cm.
*Lateral branch color.*—Green 137 C.
*Lateral branch brittleness.*—Brittle.
*Lateral branch diameter.*—2 mm.
*Branching* (*average number of lateral branches*).—Prolific with 10 breaks after pinching.
*Natural season blooming date.*—October 12-16.

Foliage:
*Leaf color.*—Upper side: Green 139A. Lower side: Green 139C.
*Color midvein.*—Upper side: Yellow-green 147D. Lower side: Yellow-green 148D.
*Size.*—Small: length 4-6.5 cm, width 2-3 cm.
*Quantity* (*number per lateral branch*).—18-20.
*Shape.*—Elliptic.
*Texture upper side.*—Sparsely pubescent.
*Texture under side.*—Pubescent.
*Venation arrangement.*—Palmate.
*Shape of the margin.*—Serrated.
*Shape of base of sinus between lateral lobes.*—Acute.
*Margin of sinus between lateral lobes.*—Diverging.
*Shape of base.*—Attenuate.
*Apex.*—Mucronulate.
*Petiole length.*—1-1.5 cm.
*Petiole diameter.*—2 mm.
*Petiole color.*—Yellow-green 147D.

TABLE 1

| Differences with the comparison variety | | |
|---|---|---|
| | 'Zanmufay' | 'Zanmusunset' |
| Start natural season flower date | October 12 (week 42) | September 14 (week 38) |
| Plant height | 35 cm | 40-45 cm |
| Plant width | 45 cm | 55 cm |

I claim:

1. A new and distinct *chrysanthemum* plant named 'Zanmufay' as described and illustrated.

* * * * *